(12) United States Patent
Takeda et al.

(10) Patent No.: US 11,087,861 B2
(45) Date of Patent: Aug. 10, 2021

(54) CREATION OF NEW CHEMICAL COMPOUNDS HAVING DESIRED PROPERTIES USING ACCUMULATED CHEMICAL DATA TO CONSTRUCT A NEW CHEMICAL STRUCTURE FOR SYNTHESIS

(71) Applicant: INTERNATIONAL BUSINESS MACHINES CORPORATION, Armonk, NY (US)

(72) Inventors: Seiji Takeda, Tokyo (JP); Daiju Nakano, Sagamihara (JP); Koji Masuda, Kawasaki (JP); Tetsuro Morimura, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 521 days.

(21) Appl. No.: 15/922,529

(22) Filed: Mar. 15, 2018

(65) Prior Publication Data
US 2019/0286791 A1    Sep. 19, 2019

(51) Int. Cl.
*G16C 20/20*    (2019.01)
*G16C 10/00*    (2019.01)
(Continued)

(52) U.S. Cl.
CPC ............. *G16C 20/20* (2019.02); *G16C 10/00* (2019.02); *G16C 20/10* (2019.02); *G16C 20/30* (2019.02)

(58) Field of Classification Search
CPC ........ G16C 20/20; G16C 10/00; G16C 20/10; G16C 20/30
See application file for complete search history.

(56) References Cited

U.S. PATENT DOCUMENTS

2003/0033088 A1\* 2/2003 Agrafiotis .............. G16C 20/60
506/5
2011/0166039 A1 7/2011 Tang et al.
(Continued)

FOREIGN PATENT DOCUMENTS

WO    2014047463 A2    3/2014

OTHER PUBLICATIONS

Igor V. Tetko, et al., "The development of models to predict melting and pyrolysis point data associated with several hundred thousand compounds mined from Patents", J Cheminform (2016) 8:2 (Year: 2016).\*

(Continued)

*Primary Examiner* — Regis J Betsch
(74) *Attorney, Agent, or Firm* — Tutunjian & Bitetto, P.C.; Randall Bluestone

(57) ABSTRACT

A computer implemented method of generating new chemical compounds is provided. The method includes preparing a data-driven substructure feature vector for each of a plurality of chemical compounds for which a chemical or physical property is known. The method further includes preparing a predefined component feature vector, creating a regression model to predict a target value for the chemical or physical property, and performing a search algorithm to identify substructure features that affect the target value for the chemical or physical property. The method further includes generating a candidate structure having the target value for the chemical or physical property, and synthesizing the candidate structure.

20 Claims, 10 Drawing Sheets

(51) Int. Cl.
  *G16C 20/10* (2019.01)
  *G16C 20/30* (2019.01)

(56) References Cited

U.S. PATENT DOCUMENTS

2017/0161635 A1  6/2017  Oono et al.
2017/0193200 A1  7/2017  Hsu et al.

OTHER PUBLICATIONS

David Koes, et al., "Enabling Large-Scale Design, Synthesis and Validation of Small Molecule Protein-Protein Antagonists", PLoS ONE, Mar. 2012 | vol. 7 | Issue 3 (Year: 2012).*
Kevin P. Murphy, "Machine Learning: A Probabilistic Perspective" Chapter 14, The MIT Press 2012 (Year: 2012).*
Rose et al., "A backbone-based theory of protein folding", PNAS vol. 103, No. 45 pp 16623-16633 (Year: 2006).*
Sun et al., "Classification of Scaffold Hopping Approaches", Drug DiscovToday. Apr. 2012 ; 17(7-8): 310-324 (Year: 2012).*
Bradley et al., "Model Melting Points Using OpenBabel," http://onschallenge.wikispaces.com/MeltingPointModel011. 2018. pp. 1-4.
Karthikeyan et al., "General Melting Point Prediction Based on a Diverse Compound Data Set and Artificial Neural Networks," Journal of Chemical Information and Modeling. vol. 45. Jan. 12, 2005. pp. 581-590.

* cited by examiner

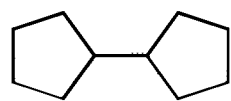
(A)
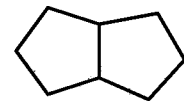
(B)
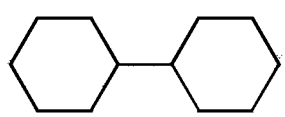
(C)
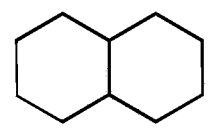
(D)
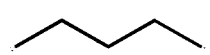
(E)
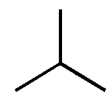
(F)
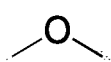
(G)
(H)
FIG. 6

FIG. 10 ORIGINAL

CREATION OF NEW CHEMICAL COMPOUNDS HAVING DESIRED PROPERTIES USING ACCUMULATED CHEMICAL DATA TO CONSTRUCT A NEW CHEMICAL STRUCTURE FOR SYNTHESIS

BACKGROUND

Technical Field

The present invention generally relates to formulating feature vectors from a plurality of known chemical structures having known properties and designing new chemical structures having desired properties using the feature vectors, and more particularly to using regression analysis and modeling to predict target properties using the feature vectors to design and synthesize new chemical compounds.

Description of the Related Art

Identifying and designing new chemical structures that have particular intended properties for synthesis can be very time consuming and expensive. Researchers can spend extensive amounts of time and effort attempting to discover new chemical compounds having a desired set of properties, but much trial and error can be involved in such research efforts. In addition, researchers can be limited by the scope of their past learning and experiences, such that the direction of their research efforts can include biases and be limited by incomplete knowledge of the huge amount of data available for known chemical structures and their properties. Use of intuition by researchers in coming up with hopeful new chemical candidates for synthesis and testing can lead researchers down unfruitful paths before sufficient familiarity and understanding of the structure/property relationships may be acquired.

SUMMARY

In accordance with an embodiment of the present invention, a computer implemented method of generating new chemical compounds is provided. The method includes preparing a data-driven substructure feature vector for each of a plurality of chemical compounds for which a chemical or physical property is known. The method further includes preparing a predefined component feature vector. The method further includes creating a regression model to predict a target value for the chemical or physical property. The method further includes performing a search algorithm to identify substructure features that affect the target value for the chemical or physical property. The method further includes generating a candidate structure having the target value for the chemical or physical property, and synthesizing the candidate structure.

In accordance with another embodiment of the present invention, a computer implemented method of generating new chemical compounds is provided. The method includes receiving input from a user selecting a property from a list of chemical and physical properties. The method further includes receiving input of a target value for the selected property. The method further includes automatically preparing a data-driven substructure feature vector for each of a plurality of chemical compounds from a data set of chemical compounds for which the selected property is known. The method further includes preparing a predefined component feature vector from backbone information, atomistic information, and bonding information. The method further includes creating a regression model to predict a resulting value for the selected property. The method further includes perform a search algorithm to identify substructure features that affect the resulting value for the selected property. The method further includes generating a candidate structure having the target value for the selected property. The method further includes synthesizing the candidate structure, and testing the synthesized candidate structure to determine the actual value of the selected property.

In accordance with yet another embodiment of the present invention, a non-transitory computer readable storage medium comprising a computer readable program for generating new chemical compounds is provided. The computer readable program perform the steps of preparing a data-driven substructure feature vector for each of a plurality of chemical compounds for which a chemical or physical property is known. The computer readable program further perform the steps of preparing a predefined component feature vector. The computer readable program further perform the steps of creating a regression model to predict a target value for the chemical or physical property performing a search algorithm to identify substructure features that affect the target value for the chemical or physical property, and generating a candidate structure having the target value for the chemical or physical property.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 6 is a diagram showing a set of predefined features used to form a predefined component feature vector, in accordance with an embodiment of the present invention;

DETAILED DESCRIPTION

Figure 1:
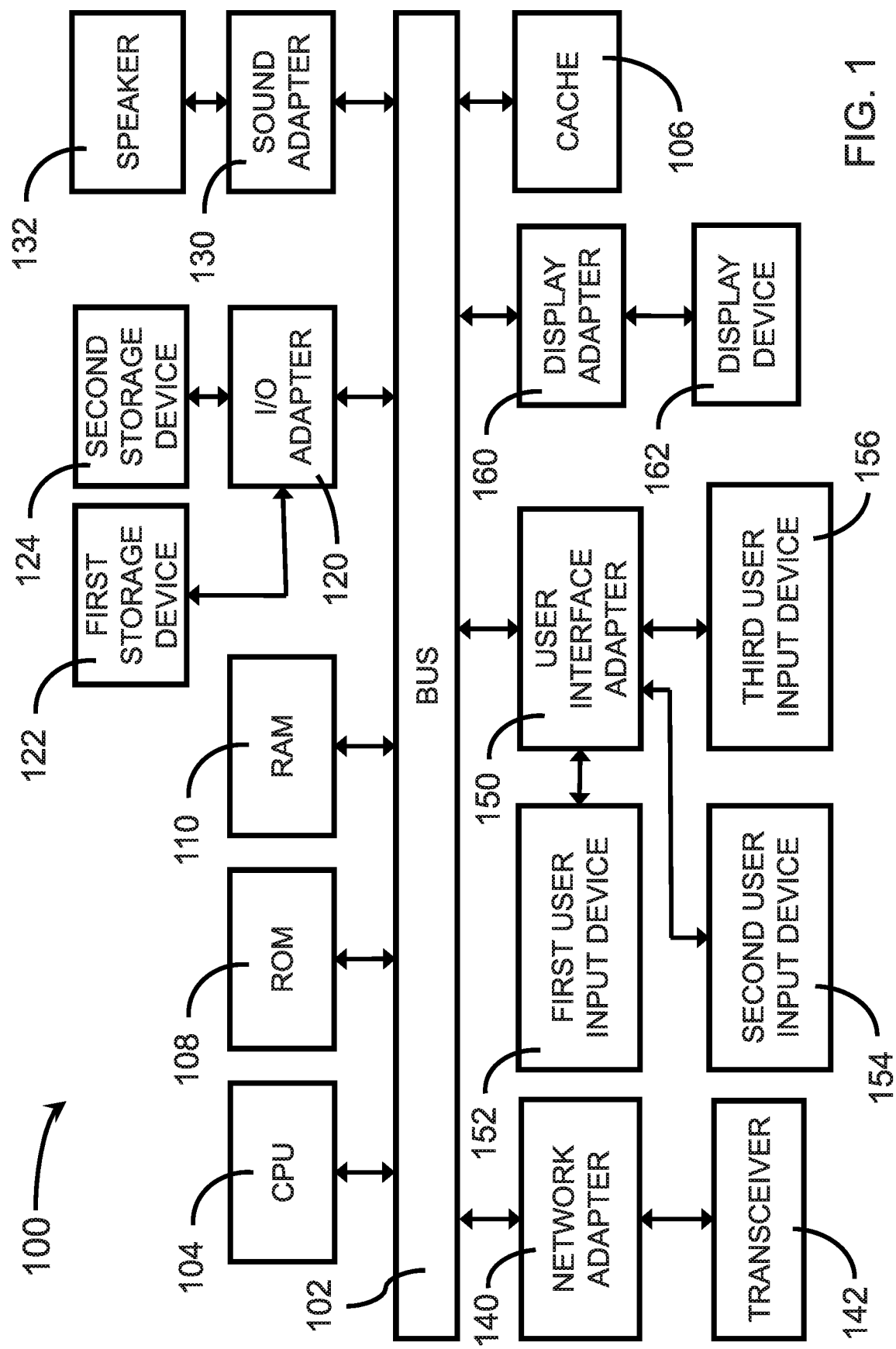
FIG. 1 is a diagram showing an exemplary processing system, in accordance with an embodiment of the present invention.

Embodiments of the present invention relate generally to the creation of new chemical compounds having desired properties using accumulated chemical data to construct a new chemical structure for synthesis. The desired properties, as identified by users, may not be available from known chemical compounds. Large amounts of data on known chemical compounds can be digested and utilized to guide research efforts towards new compounds having desired chemical and/or physical properties that were not previously available, thereby reducing or eliminating the expense of the trial and error approach or use of common sense by human researchers.

Embodiments of the present invention relate generally to automating material discovery by utilizing the known structures of materials with correlated physical and chemical properties to identify and design new materials with particular chemical structures that can provide specific intended physical and/or chemical properties. Feature vectors for known chemical compounds can be automatically generated by manipulating character strings representing each molecular structure.

Embodiments of the present invention relate generally to utilizing feature extraction processes to identify components of a chemical structure, correlating the chemical components to a desired physical and/or chemical property, determining which of the components can contribute to a desired property, formulating potential new chemical structures having the desired physical and/or chemical properties, filtering the potential new structures to identify a specific new structure having the desired physical and/or chemical properties, and synthesizing the specific new structure.

Embodiments of the present invention relate generally to obtaining a plurality of chemical structures for which correlated data on one or more desired properties is known and preparing a feature table that identifies the substructures (e.g., backbone, chemical moieties, heteroatoms, etc.) comprising each chemical compound structure. Using the known values for each of the chemical and/or physical properties, the table of identified substructures can be analyzed through regression analysis to correlate the contribution of the structural features to the resulting chemical and/or physical properties without reliance on an expert's cognitive processes.

Embodiments of the present invention relate generally to specifying the value of one or more desired chemical and/or physical properties that is not provided by the available set of chemical structures, and generating a new structure having the specified values of the one or more desired chemical and/or physical properties.

Embodiments of the present invention relate generally to preparing data-driven feature vectors for a set of chemical structures using an exhaustive analysis, for example, a Morgan Fingerprint approach, and a reference (predefined) feature vector for a fixed catalog of chemical building blocks (e.g., chemical moieties/substructures), and using the data-driven feature vectors and reference (predefined) feature vector to generate candidate molecular structures, where the generated structures are filtered at one or more stages of the candidate structure generation.

Exemplary applications/uses to which the present invention can be applied include, but are not limited to: pharmaceutical drug discovery, biological drug discovery, materials synthesis, polymer synthesis, and inorganic compound synthesis.

Referring now to the drawings in which like numerals represent the same or similar elements and initially to FIG. 1, an exemplary processing system is shown, in accordance with an embodiment of the present invention.

An exemplary processing system 100 to which the present invention may be applied is shown in accordance with an embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, can be operatively coupled to the system bus 102.

A first storage device 122 and a second storage device 124 can be operatively coupled to system bus 102 by the I/O adapter 120. The storage devices 122 and 124 can be any of a disk storage device (e.g., a magnetic or optical disk storage device), a solid state device, a magnetic device, and so forth. The storage devices 122 and 124 can be the same type of storage device or different types of storage devices.

A speaker 132 can be operatively coupled to system bus 102 by the sound adapter 130. A transceiver 142 can be operatively coupled to system bus 102 by network adapter 140. A display device 162 can be operatively coupled to system bus 102 by a display adapter 160.

A first user input device 152, a second user input device 154, and a third user input device 156 can be operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
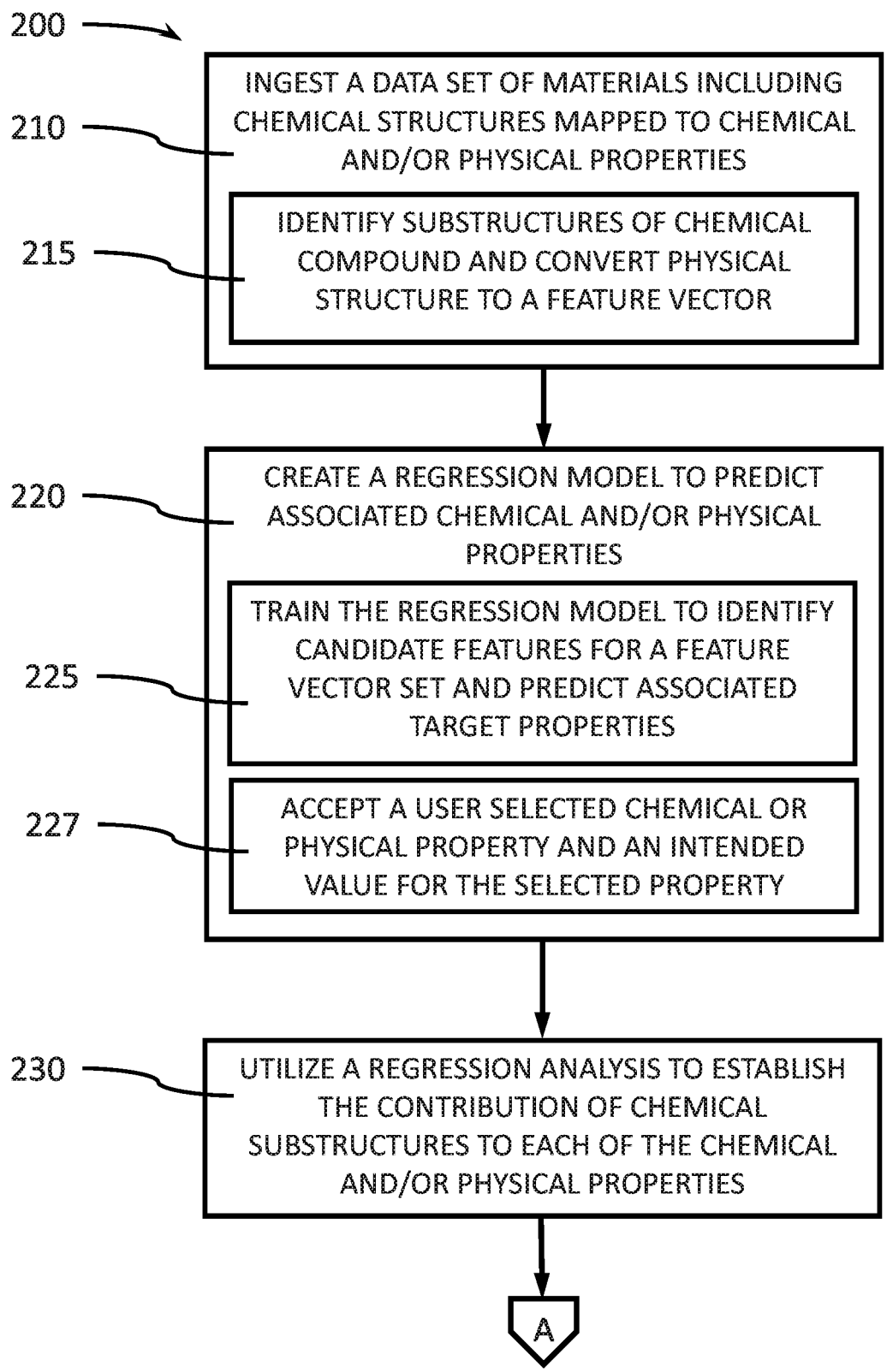
FIG. 2 is a block/flow diagram showing a general algorithm for transforming a material data set including chemical structures with associated properties to a new material, in accordance with an embodiment of the present invention.

FIG. 2 is a block/flow diagram showing a general algorithm for transforming a material data set including chemical structures with associated properties to a new material, in accordance with an embodiment of the present invention.

Most chemical properties are affected by substructures included in the chemical structure of a compound (e.g., organic molecules, biological compounds, inorganic compounds, polymers, etc.). Regression analysis and modeling can be used to identify the contribution of separate substructure(s) in a compound to a specific property through analysis of a large data set of chemical compounds including the particular substructure(s). The converting of the chemical structures to feature vectors, regression analysis and modeling, and filtering of new candidate structures can be driven by data and automated analysis rather than human experience, as shown in process algorithm 200.

In block 210, a data set of materials including a plurality of chemical structures and chemical and/or physical properties associated with each of the chemical structures can be stored in computer memory, for example, in a database or on storage discs. The data set of materials can be accessed by a processing system 100 for automated analysis. The data set of materials can be in a digital format accessible by a processing system.

In one or more embodiments, a feature vector can be created for each chemical compound in the data set of materials by counting the number of each of all the possible specific substructure permutations identified in the chemical compound structure. Two different types of feature vectors can be created. The first type of feature vector can include a data-driven substructure count, and the second type of feature vector can include a predefined component count. Each feature vector can include values for the quantity of each identified substructure for a single chemical compound. The identity of each of all the possible specific substructure permutations for a single chemical compound can form a data-driven substructure set.

In block 215, the data-driven substructure feature vector can be created by identifying the substructures of each chemical compound in the data set. Creation of the data-driven substructure feature vector can include identifying all of the possible ways a chemical structure can be subdivided with the atoms of the chemical compound represented as nodes and bonds represented as edges of a graph. The identified substructures can be recorded using simplified molecular-input line-entry system (SMILES). SMILES is a string obtained by printing the symbols for the nodes encountered in a depth-first tree traversal of the chemical graph. The chemical graph is first trimmed to remove hydrogen atoms and cycles are broken to turn it into a spanning tree. Where cycles have been broken, numeric suffix labels are included to indicate the connected nodes. Parentheses are used to indicate points of branching on the tree. Other chemical table file formats can also be used, for example, MDL Molfile and structure-data file (SDL). The data-driven substructure feature vector can be automatically created from the chemical data set using a processing system 100.

The data-driven feature is powerful for modeling the relationship between molecular structure and associated property, but a full structure may not or cannot be decoded by using this approach alone because some substructures may be independent, but some substructures may be partially overlapping. The data-driven features can be utilized as a structural filter for structures generated using pre-defined features.

Counts of substructures do not provide information about their connections (e.g., bond type) nor the extent of their overlapping (e.g., sharing of the same nodes and/or edges), therefore a molecule cannot be built from the individual substructures. Information about building components of a molecule from which a molecular structure can be directly generated can be introduced using the feature vector of pre-defined components and counts. A data-driven substructure feature set and a pre-defined component feature set can be used together to generate structures, and the data-driven features can work as a structural filter for structures generated by the pre-defined features.

A predefined component count for the second type of feature vector can be created from predefined building blocks intended to be analyzed and used to generate the new chemical compound. Predefined substructures can provide information about three types of components: backbone, atoms, and bonds. The predefined building blocks can be substructures, including, but not limited to, heteroatoms (e.g., nitrogen (N), oxygen (O), sulfur (S), halogens (e.g., fluorine (F), chlorine (Cl), bromine (Br), etc.), etc.), aromatic rings (e.g., benzene), aliphatic rings (e.g., cyclopentane, cyclohexane, etc.), functional groups, (e.g., carbonyl (C=O), carboxylic acid (—COOH), alcohols (—OH), amines (—$NH_2$), amides (—CONH—), thiols (—$SH_2$), double bonds, triple bonds, the total number of atoms and/or each type of atom, backbone length/structure, etc. The predefined building blocks can be defined such that they do not overlap. The predefined component feature vector can be created by identifying a quantity for each of the predefined building blocks. The identity of each of the predefined component can form a predefined component set.

In block 220, a regression model can be created to correlate the known chemical structures and substructures to the known chemical and/or physical properties of the chemical compounds. The regression model can be used to predict associated chemical and/or physical properties from the substructures. An independent regression model can be created to predict each property.

A regression model, F, can be built to predict a target property, y, from an identified set of substructures, where F: ↦y, where x is a concatenated feature vector x:=($X_D^{Select}$, $x_P$), and y is the property. The type of regression model, F, utilized can depend on both the type of material(s) identified and the target properties selected. A regression model can be independently created for each property as $F_1:x_1 \mapsto y_1$, $F_2:x_2 \mapsto y_2$, etc. The regression analysis may utilize any regression method to provide adequate accuracy, for example, a kernel ridge regression method, where the type of regression method selected may affect the total final accuracy of the predicted resulting value. In case that multiple chemical and/or physical properties are targeted, x, is a sum-set of ω for property $y_j$ given as $x = x^{(j)} \cup_{j=1}^{N} x^{(j)}$, where j is an index from 1 to the number of properties selected, and $x^{(j)}$ for is the $j^{th}$ substructure that can contribute to the $j^{th}$ property, $y_j$.

In block 225, the regression model can be trained using known materials and properties to identify candidate features for a feature vector set and predict the associated target properties.

After sufficiently training the regression model, the model can obtain a candidate feature vectors set that can satisfy a user's query for selected properties with targeted values.

In block 227 a user can select a chemical or physical property that the user intends to use as a reference for identifying a new chemical structure. The chemical or physical property can be selected from a list of chemical/physical properties. The processing system can receive the selected chemical or physical property and use the property in the search algorithm. One or more properties can be selected by the user. A sum-set of $^{(j)}$ for all the selected properties $y_j$ can be utilized.

Physical properties can include, but not be limited to, melting point, freezing point, triple point, vapor pressure, heat capacity, refractive index, dielectric constant, resistivity, viscosity, glass transition temperature, thermal conductivity, coefficient of thermal expansion, elasticity/plasticity, and tensile strength. Physical properties can be measured independent of the desired chemical compound's environment or interaction with another material.

Chemical properties can include, but not be limited to, toxicity, standard enthalpy of formation, hydrophilicity/hydrophobicity, surface energy, pH, and dipole moment. Chemical properties can involve interactions between the desired chemical compound and another material.

The user can input a desired value for each selected property, which can be received by the processing system, for use in the regression analysis and search algorithm. The inputted value can be a value different from the known values for the identified property associated with the known chemical compounds in the data set. The new set of values can be used to guide the development of a new compound having the new values.

In a non-limiting exemplary embodiments, a user can select melting point as the physical property and surface energy as a chemical property for a new compound, and input a desired value for the melting point and the surface energy. A set of chemical structures with known substructures, known surface energy, and known melting points can be analyzed to determine the contributions (e.g., weighting coefficients) of each substructure to the properties. The contributions of the substructures can be determined through regression analysis and modeling by creating feature vectors for each of the chemical structures in the set, where the different known melting points can be back-calculated in view of the substructures in each chemical compound. The inputted value for the new melting point can then be used to identify and combine the various substructures to arrive at a new final structure having the desired value for the melting point. This can also be done for the surface energy.

In block 230, the regression model can be used to analyze the contribution of the different substructures and backbone and bonding arrangements to a particular chemical or physical property, and establish weighting coefficients for each of the chemical substructures (e.g., moieties). Information regarding the effect of the different substructures on a particular property can be used to identify substructure components for assembling a new chemical structure having a desired value for the property. The contributions of the substructures to the property value can be optimized to identify a particular chemical structure for synthesis and testing.

A regression model that uses an L1 regularization technique is called a Lasso Regression. Regularization is a process applied to objective functions of introducing additional information in order to prevent overfitting data points in arriving at a predicted function. $\lambda$ is a parameter which controls the importance of the regularization term. A regression model can automatically detect patterns in data, for example, the relationship between substructures in a chemical compound and a chemical or physical property, and then use the uncovered patterns to predict future outcomes. The L1 regularization can select effective substructures from a first set of chemical compounds.

A regression model that uses L2 regularization technique is called a Ridge Regression, where the difference between the L1 regression and the L2 regression is the form of the penalty term. L2 regularization can be applied to a second set of chemical compounds.

The second portion of the process generates a new chemical structure from the analyzed structures by identifying the various substructures that contribute at least a portion to the identified property value. The weightings of different types of substructures to the property value can be used to design a chemical structure with the intended final value through a reverse process from the regression analysis. The new chemical structure is, thereby, designed by starting with desired chemical and/or physical properties and combining substructures that affect the desired chemical and/or physical properties to arrive at a final chemical structure.

Figure 3:
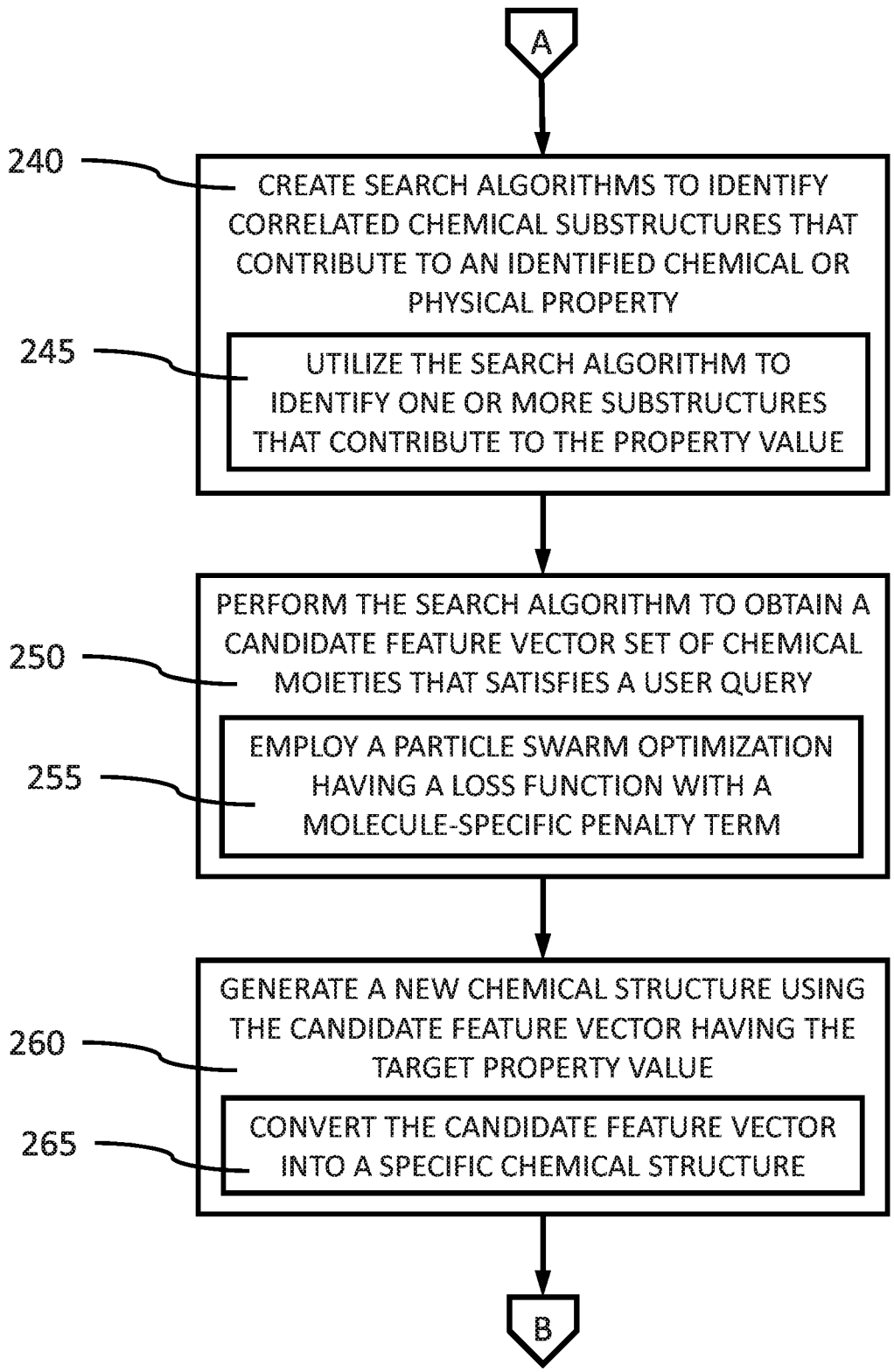
FIG. 3 is a continuation of the block/flow diagram of FIG. 2, in accordance with an embodiment of the present invention.

FIG. 3 is a continuation of the block/flow diagram of FIG. 2, in accordance with an embodiment of the present invention.

In block 240 a search algorithm can be created to identify chemical substructures that contribute to an identified chemical or physical property.

While a regression analysis can be used to identify the correlation between given chemical structure(s) and set(s) of substructures with a particular property and value utilizing, $F: x \mapsto y$, finding a set of substructures that can be assembled into a chemical compound having one or more properties with predefined values can be much more difficult. Candidate feature vectors that satisfy user-set target properties can be identified using a search algorithm rather than solving for the inverse function, $F^{-1}$. In various embodiments, a particle swarm optimization (PSO) algorithm with a penalty term for molecular constraints can be used, where PSO is a population based stochastic optimization technique. PSO is a computational method that optimizes a problem by iteratively trying to improve a candidate solution with regard to a given measure of quality.

In block 245, the search algorithm can be utilized to identify the substructures that contribute to the property's value. The substructures can be combined to arrive a new chemical structure based on optimization of the property value utilizing the identified substructures and arrangements. The identified substructures can be from the data-driven substructure feature vector and predefined component feature vector using the data-driven substructure set and predefined component set.

In block 250, the search algorithm can be performed to obtain a candidate feature vector set of chemical substructures that satisfies the user's query. A complete set of features can be created for generating the new chemical structure. The structure can be encoded into SMILES.

One or more candidate chemical structures can be generated from each feature vector, $x_P$, generated by the search algorithm, such that they provide satisfactory target values. Candidate structures can be generated by referring to substructures identified in a process including backbone structuring, atomistic (also referred to as "atomic") detailing, and bond detailing.

In block 255, the search algorithm can employ a particle swarm optimization (PSO) having a loss function component with a molecule-specific penalty term. Optimization of the search function can narrow the chemical structure down to structures having a predicted property value closest to the user input value.

In block 260, a new chemical structure can be generated from the candidate feature vector having the property value closets to the desired value, as input by the user.

Backbone structuring can refer to the graph topology of a chemical structure without atomistic or bonding details in conformity with the rules of SMILES grammar. Graph nodes can be individual carbon atoms, C. Configurations and connections of rings (e.g., 5-membered and 6-membered) can be included, as well as linear and branched chains of carbons, C. Rings can be identified as bonded or fused. A possible connection sequence of the backbone structure can be generated from these components, where the arrangement can satisfy the requirement that a total number of atoms and a correct number of rings be represented. The connection sequence can be encoded in SMILES grammar.

Atomistic detailing can include specifying the correct number and arrangement of heteroatoms (i.e., atoms other than carbon and hydrogen), in and along the backbone structure.

Bonding detailing can include specifying the correct number and arrangement of chemical bonds other than single bonds (e.g., double bonds, triple bonds, and aromatic rings).

Actual chemical structures can be generated using the above process, but the number of possible structures increases exponentially (e.g., $10^1$-$10^2$) at each step due to the different available positions and connections of each new detail or modification, as represented by a position in a SMILES string.

In block 265, the candidate feature vector can be converted into a specific new chemical structure by identifying the number and arrangement of the chemical substructures output by the processing system from the search algorithm.

The generated candidate structures can be filtered at each step to eliminate candidate structures and/or substructures that have no or a negligible effect on a particular property. Each substructure can transform its own shape such that it becomes useful as a filter. The substructures can be modified to represent the actual substructures that can be assembled to form the new chemical compound. The substructures can initially be modified by generalizing all substructures to represent heteroatoms and chemical bonds as carbon atoms and single bonds for backbone structuring, since the additional atomistic and bonding details are not utilized at that step. The additional atomistic and bonding details can be reintroduced at the subsequent stages of the structure generation process. The atomistic details can be reintroduced by replacing the carbon atoms in the substructures remaining after the first round of filtering with the heteroatoms at their original positions in the substructures. A second stage of filtering can then be applied to the substructures containing the additional atomistic details to eliminate substructures that are not applicable. The bonding details can then be reintroduced to the substructures remaining after the second stage of filtering. The number of possible chemical structures can be suppressed by each stage of filtering. The candidate structures can be filtered using the counts of substructures appearing in $X_D^{Select}$.

Figure 4:
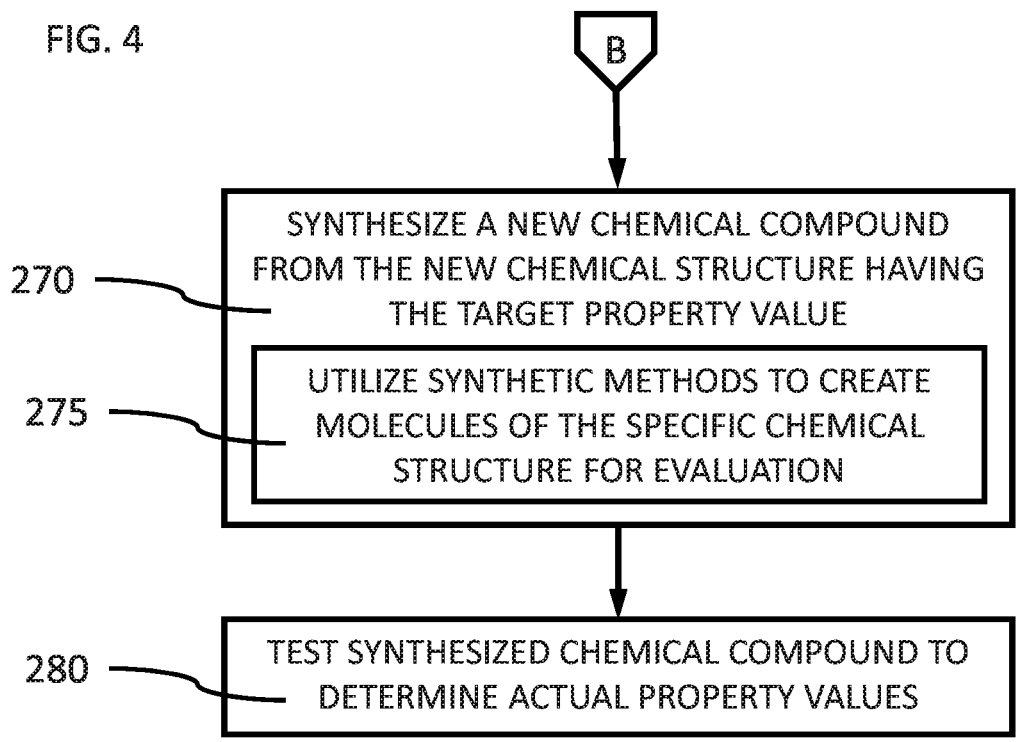
FIG. 4 is a continuation of the block/flow diagram of FIG. 3, in accordance with an embodiment of the present invention.

FIG. 4 is a continuation of the block/flow diagram of FIG. 3, in accordance with an embodiment of the present invention.

In block 270, the new chemical compound can be synthesized from the new chemical structure having the target value for the chemical or physical property.

In block 275, the newly generated chemical structure can be synthesized for testing and use using various synthetic methods. The new chemical structure can be used to prepare a synthetic pathway for making the new chemical compound.

In block 280 the synthesized chemical compound can be tested using various analytical and instrumental methods to determine the actual values for the selected chemical and/or physical properties. The testing can determine if the synthesized compound has the property values utilized in generating the candidate structure(s) and/or identified as the target value(s).

Figure 5:
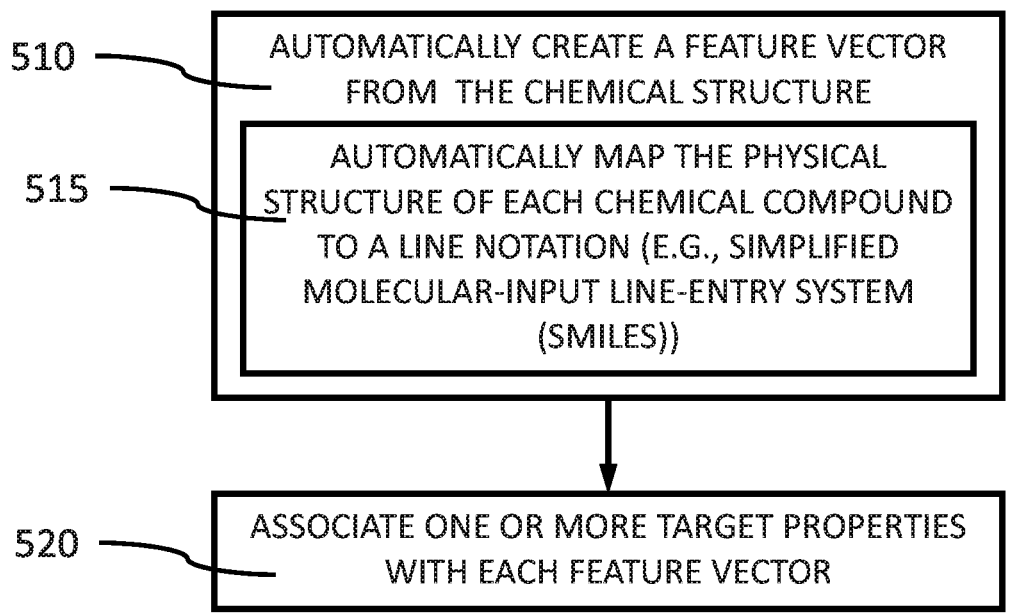
FIG. 5 is a block/flow diagram showing a method of creating a feature vector, in accordance with an embodiment of the present invention.

FIG. 5 is a block/flow diagram showing a method of creating a feature vector, in accordance with an embodiment of the present invention.

A feature vector can capture the known chemical compound's features in an accurate manner, where the feature vector can represent all of the possible chemical compound substructures without biasing the representation towards particular functional groups or backbone configurations.

In block 510, a representation of the chemical structures as feature vectors can be automatically generated using feature extraction based on known chemical bonding properties and identifiable functional groups without direct human input to define the substructures. The generated substructures for the feature vector can be recognized by users as functional groups and backbone structures utilized in the chemical arts to describe and synthesize new compounds. The substructures for the feature vector can also be recognized by users as features that affect known physical and chemical properties.

The feature vectors can be of two different types. A first type of feature vector can include substructure counts that determines and records the number of each substructure identified in each chemical compound through the automatic process from the data set of chemical compounds. The automatically generated set of substructures and counts can include segments of a chemical compound that do not correspond to a readily identifiable functional group or backbone structure.

A second type of feature vector can include substructure counts that determines and records the number of each substructure identified as a known functional group or backbone structure in the chemical compound, such that the substructures can potentially generate new structures that are more easily identifiable and synthesizable by a user.

In block 515, for the first type of feature model, let $M=\{m_1, m_2, m_3, \ldots, m_{n-1}, m_n\}$, where M is a set of the chemical compounds, $m_i$, where i is an index=1 to n, and n is the total number of molecules included in the data set of chemical compounds. The structure and substructures of a chemical compound, $m_i$, can be analyzed to automatically identify sets of substructures for each chemical compound. Let $\mathcal{S}_m=\{s_{i,1}, s_{i,2}, s_{i,3}, \ldots, s_{i,k}\}$, where $\mathcal{S}_m$ is a set of elements, $s_{i,j}$, where i is the index of the chemical compound, and j is an index=1 to k for the substructures of the identified compound, $m_i$. $\mathcal{S}_{1,j}$, can be the set $\{s_{1,1}, s_{1,2}, s_{1,3}, \ldots, s_{1,n}\}$ of the actual substructures of chemical compound $m_1$. In various embodiments, $\mathcal{S}_m$ can be an exhaustive set, $\mathcal{S}^{full}$, such that $\mathcal{S}_m$ includes all possible substructure representations for a chemical compound, $m_i$, from the individual atoms up to the entire molecule. The substructures can be identified using rules that identify all the possible permutations of atoms and bonds between the atoms for a chemical compound. In various embodiments, a Morgan Fingerprint approach can be used in preparing data-driven feature vectors for a set of chemical structures using an exhaustive analysis.

An exhaustive (i.e., complete) set, $\mathcal{S}^{full}$ of substructures can be created for the set of chemical compounds, M, in the data set, where $\mathcal{S}^{full}=\cup_{i=1}^{N}{}^{(i)}$, where N denotes the number of chemical compounds.

In one or more embodiments, an exhaustive set, $\mathcal{S}^{full}$, for an entire set, M, of molecules, can be represented as $\mathcal{S}^{full}=\cup_i{}^{(i)}$, for i=1 to N. In other words, by expanding the elements of $\mathcal{S}^{full}$ to be $\mathcal{S}_1^{full}, \mathcal{S}_2^{full}, \mathcal{S}_3^{full}, \ldots$ a vector for the chemical compound, $m_i$, can be represented as $X_D^{(n)}:= (N_D(m_i, \mathcal{S}_1^{full}), (N_D(m_i, \mathcal{S}_2^{full}), (N_D(m_i, \mathcal{S}_3^{full}), \ldots )$. $X_D^{(n)}$ represents the topological feature of a molecular structure by incorporating the counts of all partial graphs appearing in $m_i$. Due to the exhaustiveness, the information in $X_D^{(n)}$ includes substantial redundancy. For example, most of the substructures in $\mathcal{S}^{full}$ may appear only once or a few times even in the full molecules set M; therefore, using them all may not be suitable.

Let $N_D=\{n_{1,1}, n_{1,2}, n_{1,3}, \ldots, n_{1,j}\}$, where $n_{i,j}$ is the quantity of each identified substructure, $s_{i,j}$, of a first chemical compound $m_i$.

A molecular structure and a substructure can be represented as graphs composed of nodes (atoms) and edges (chemical bonds), $\mathcal{S}_m=\{s_{i,1}, s_{i,2}, s_{i,3}, \ldots, s_{i,k}\}$ can form a partial graph of $m$.

To select only the substructures that affect the target property, a feature selection process can be performed on it. By denoting the target property as t, a LASSO (Least Absolute Shrinkage and Selection Operator) regression model $\mathcal{L}: x_D \mapsto y$ can be created. Tuning the hyperparameter (degree of $L_1$ penalty term) and setting a threshold $w_{th}$ for absolute value of regression coefficient $|w|$, the system selects important substructures. We denote the set of selected substructures as $\mathcal{S}^{Select}$, and corresponding feature vector as $X_D^{Select}$. $\mathcal{S}^{select}$ can be referred to as a data-driven substructure feature set and $X_D^{Select}$ as the data-driven substructure feature vector. The substructure selection can be accomplished by L1 regularization to select effective substructures. L2 regularization can be utilized for substructure selection for the predefined components of the predefined component set.

A final structure set can be a concatenation of a data-driven substructure feature set and a predefined component feature set, $x:=(X_D^{Select}, x_P)$.

A deep neural network (DNN) may not be the best choice. In material industries generally the extent of available data can be much smaller (typically in ranges on the order from $10^2$ to $10^3$ data points) than the case of object recognition, speech recognition, text mining and so on, and therefore the high representative power of a DNN can bring on the problem of over fitting.

There may be exceptions for target properties that are low level (i.e., atomistic level properties such as energy bandgap etc.), not mesoscopic molecular level or macroscopic functional level (e.g., luminescent efficiency), so that the properties of the myriad number of chemical compounds can be calculated by physical simulation (e.g., DFT simulation).

In one or more embodiments, the predicted chemical structure can be synthesized to provide a physical organic molecule, inorganic compound, polymer, or other chemical for testing and review of the resulting properties. The organic molecule(s) may be synthesized using known organic preparatory methods available to chemists. Polymers may be prepared by synthesizing the organic monomer using known organic preparatory methods and polymerizing the resulting monomer to produce the polymer. Inorganic compounds may be synthesized using known inorganic preparatory methods.

In various embodiments, the resulting chemical compound can be tested to determine if the compound has the desired value for the intended physical or chemical property.

FIG. 6 is a diagram showing a set of predefined features used to form a predefined component feature vector, in accordance with an embodiment of the present invention.

In one or more embodiments, backbone components of the predefined feature vector can include, for example, substructures: (A) bonded 5-member rings, (B) fused 5-member rings, (C) bonded 6-member rings, (D) fused 6-member rings, (E) linear bonded carbon chains, (F) branched bonded carbons, (G) ether bond, and (H) alcohol groups.

Figure 7:
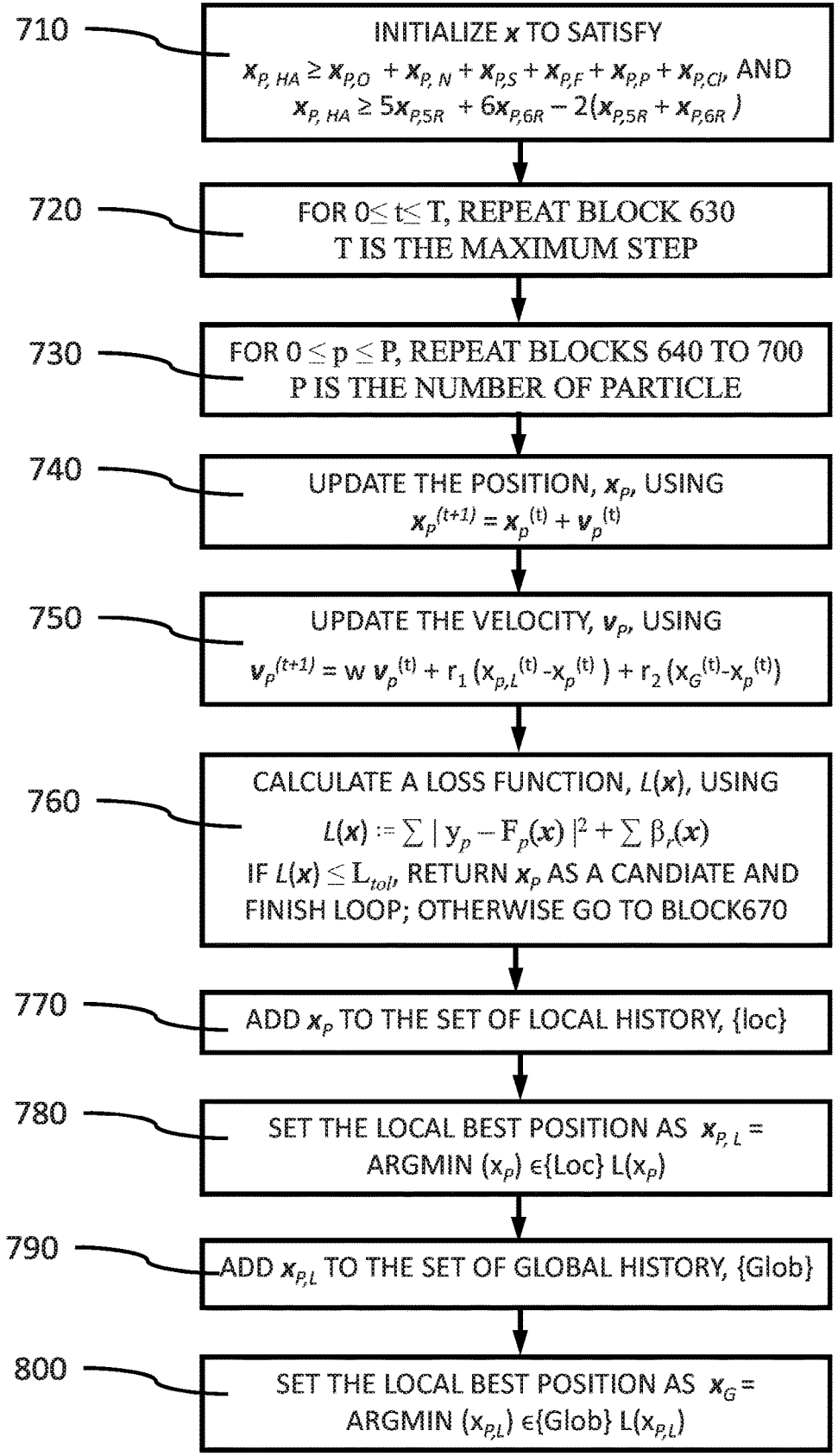
FIG. 7 is a block/flow diagram showing a particle swarm optimization algorithm in a chemical space, in accordance with an embodiment of the present invention.

FIG. 7 is a block/flow diagram showing a particle swarm optimization algorithm in a chemical space, in accordance with an embodiment of the present invention.

Identifying candidate feature vectors that satisfy user-selected target properties can be difficult due to non-linear aspects of an inverse regression model, $F^{-1}$, so a search algorithm can be employed rather than directly solving $F^{-1}$. Since the plane $\mathcal{F}(x)$ has multiple peaks with local minima and the search space x is discrete, a gradient method may not be appropriate. Instead, a particle swarm optimization (PSO) algorithm with a penalty term for molecular constraints can be employed. A target structure having a predetermined value for a selected chemical or physical property can be identified by iteratively trying to improve a candidate solution with regard to a given measure of quality, for example, the closeness of the calculated value for the selected property from the input value the problem, where the problem can be solved by having a population of candidate solutions. Each particle, a candidate substructure, can iteratively change position (e.g., transform) and velocity to minimize the loss function while being guided by local minima and a global minimum.

In various embodiments, a new chemical compound can be generated using a particle swarm optimization algorithm with a penalty term for chemical structure constraints.

In block 710, by initializing a search space, x, to satisfy $x_{P,HA} \geq x_{P,O}+x_{P,N}+x_{P,S}+x_{P,F}+x_{P,P}+x_{P,Cl}$, where 'P' denotes "Predefined" substructures, that is in contrast to "Data-driven" substructures, as denoted by 'D' in $x_D$. HA is the number of atoms in the chemical compound other than hydrogen, O is the number of oxygen atoms, N is the number of nitrogen atoms, S is the number of sulfur atoms, F is the number of fluorine atoms, P is the number of phosphorus atoms, and Cl is the number of chlorine atoms. Other heteroatoms (i.e., atoms other than carbon and hydrogen) can be included in the formula to account for atoms in the chemical compounds and/or predefined component feature vector. The PSO can be initialized with a group of random particles (solutions) and then searches for optima by updating generations.

In block 720, repeat block 630 for $0 \leq t \leq T$, where t is a step index, and T is the maximum interation for the PSO in the search space. The searching is a repeated process, with a stop criteria that the maximum iteration number is reached or the minimum error condition is satisfied.

In block 730, repeat blocks 640 to 700 for $0 \leq n \leq N_P$, where n is a particle index, and $N_P$, is the number of particles.

In block 740, there can be an update to a position, $x_P$, where $x_P^{(t-1)}=x_P^{(t)}+v_P^{(t)}$; where "position" (also referred to as "location") is a particle's position in the search space that is defined by the feature vector, $x_P$ or $x_D$, as applied in Particle Swarm Optimization. The "particle" can be a potential solution to the presented problem by moving through the problem space by following the current optimum particle (solution). Each single solution is a particle in the search space.

In block 750, there can be an update a velocity, $v_P$, where $v_P^{(t+1)}=w\, v_p^{(t)}+r_1(x_{P,L}^{(t)}-x_p^{(t)})+r_2(x_G^{(t)}-x_p^{(t)})$, where $r_1$ and $r_2$ are random values between 0 and 1, and the velocity is the extent to which a particle (solution) in the search space can move (evolve) towards a value in a step. The current velocity $v^{t+1}$ is computed by adding two components to the previous velocity vt of the particle. The first component is the difference between the current position x of the particle and the position p with the best value obtained by the particle. The second component is computed by the difference between the current position x of the particle and the position g of the best known value of all the particles in the swarm.

In block 760, there can be a calculation of a loss function $L(x_P)$, where $L(x_P):=\Sigma|y_p-F_p(x)|^2+\Sigma\beta_r(x)$, where if $x_P$ is less than $L_{tol}$, identify $x_P$ as a candidate position of a substructure, where $y_p$ and $\mathcal{F}_p(x)$ are targeted and predicted values for property $y_p$, respectively, and $\beta_r(x)$ is the penalty term for a restriction rule, r. $L_{tol}$, is the tolerance for the answer, where the PSO searches for an $x_P$ that makes a loss function equal to or as close to zero (0) within the tolerance, $-L_{tol}<L(x)<+L_{tol}$. Here $y_p$ is a targeted value and $F_p(x)$ is a predicted value for property p.

In block 770, $x_P$ can be added to a set of local history, where the local history can be a list of the best positions (values) that each particle previously found.

In block 780, set the local best position to $x_{P,L}=\text{argmin}_{(xP)\epsilon_{\{Loc\}}}L(x_P)$, where $L(x_P)$ is the loss function applied to $x_P$, and $\epsilon_{\{Loc\}}$ is a set of best positions. The local best position is reset to the best position of the ones listed in the local history.

In block 790, add $x_{P,L}$ to a set of global history, {Glob}, where the global history records the overall best position in the local history.

In block 800, set a global position as $x_G=\text{argmin}_{(xP,L)\epsilon_{\{Glob\}}}L(x_{P,L})$, where $\epsilon_{\{Glob\}}$ is a set of overall best positions. The global best position can be reset to the best position of the ones listed in the global history. The best solution relative to all other solutions can be identified as a best solution.

For $0\le n\le N_P$, where $N_P$ is the total number of particles, and the particles are the representations of the feature vectors of a candidate molecular structure, repeat updating the position, updating the velocity, and updating the loss function calculation for subsequent particle (substructure).

For $0\le t\le T$, where T is the maximum step, repeated for updating the position, velocity, loss function calculation, and storage of local and global positions. The sequence can be repeated to obtain a plurality of feature vector candidates, and a candidate structure generated from each feature vector.

Figure 8:
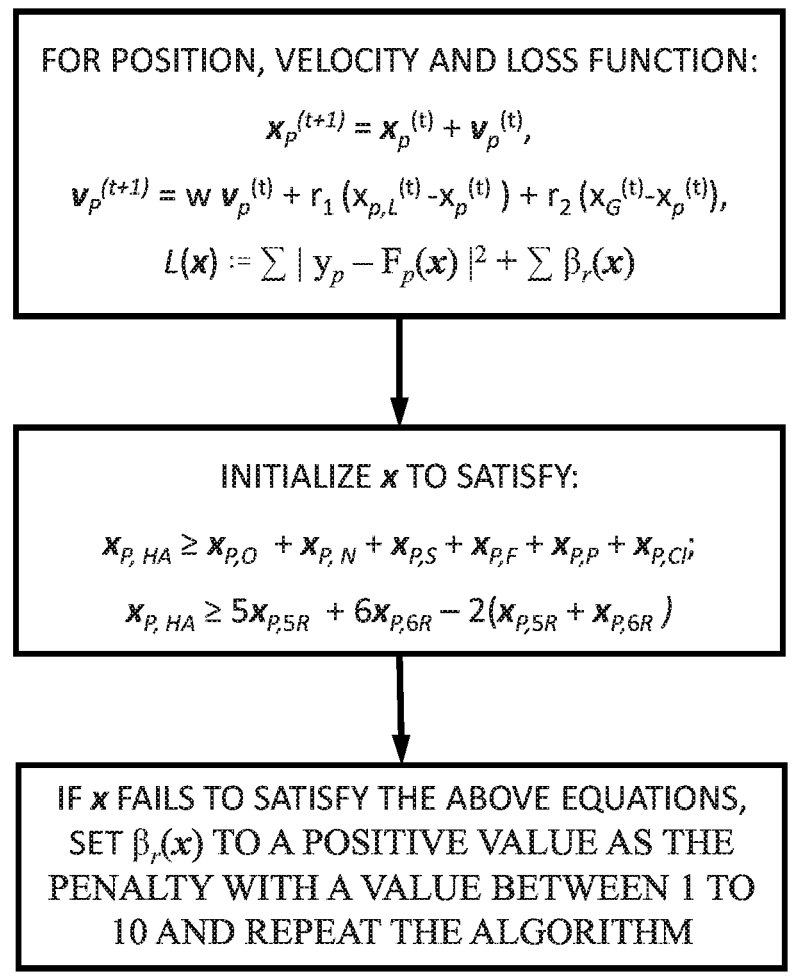
FIG. 8 is a block/flow diagram of the particle swarm optimization details and equations, in accordance with an embodiment of the present invention.

FIG. 8 is a block/flow diagram of the particle swarm optimization details and equations, in accordance with an embodiment of the present invention.

Figure 9:
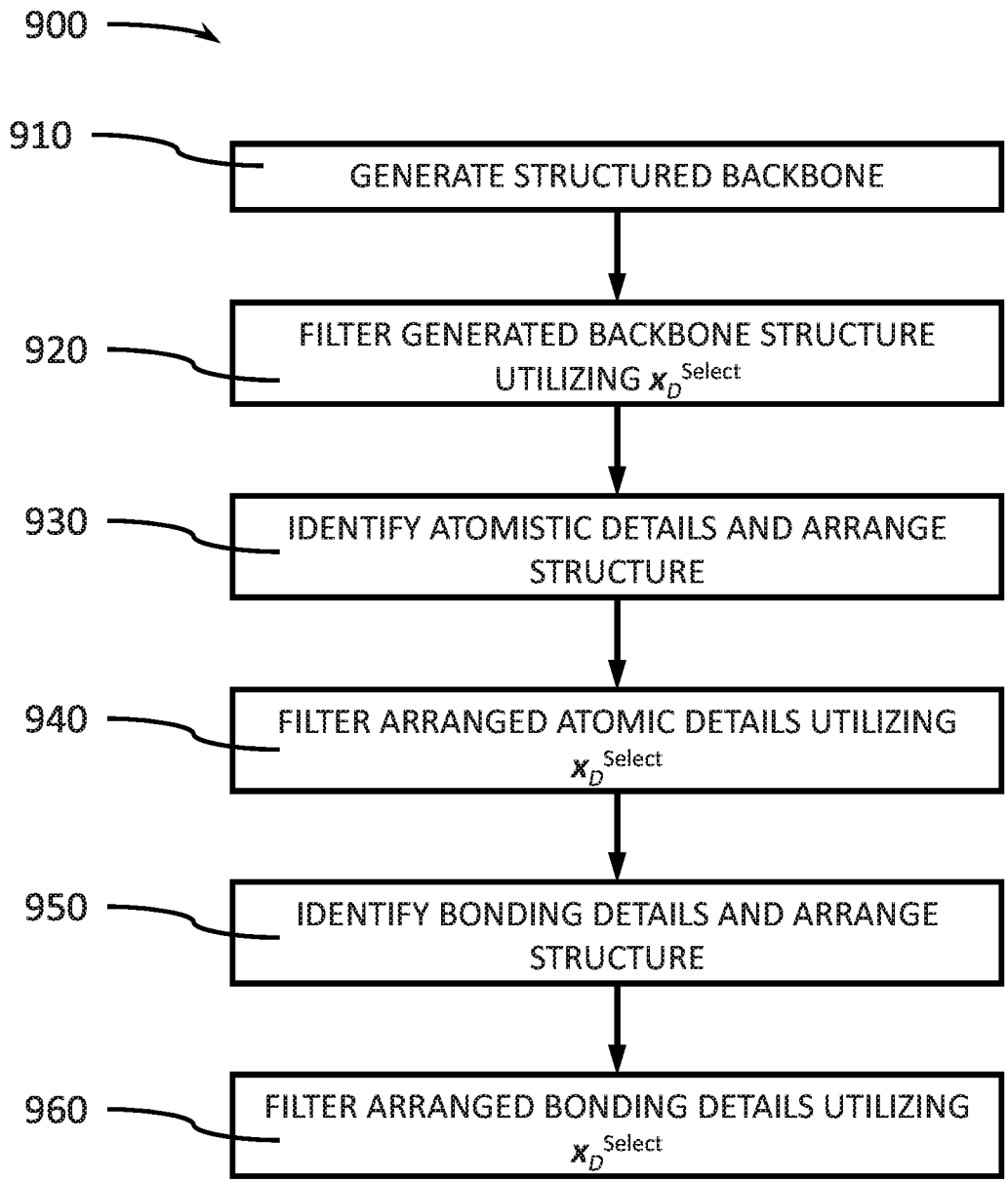
FIG. 9 is a block/flow diagram showing a structure generation algorithm, in accordance with an embodiment of the present invention.

FIG. 9 is a block/flow diagram showing a structure generation algorithm with filtering, in accordance with an embodiment of the present invention.

Substructure generation using a structure generation algorithm 900 with filtering can include transforming and filtering identified substructures to reduce the total number of possible candidate structures to be generated and analyzed. Candidate molecular structures can be generated from each feature vector x such that the feature vectors satisfy values of both of $x_D^{select}$ and $x_p$.

In block 910, a structured backbone is generated, where possible connection sequences of the identified components satisfy the specifications of $x_{P,HA}$, $x_{P,5-R}$, and $x_{P,6-R}$. A SMILES sequence can be generated from the generated backbone structure.

In block 920 the structured backbone is filtered using generalized substructures. Using the counts of substructures appearing in $x_D^{Select}$, generated structures can be filtered to eliminate substructures that are not applicable to the generation of later substructures after introduction of additional details (e.g., atomistic and bonding), for example, substructures that could not include identified oxygen atoms or double bonds can be eliminated as potential substructures for a candidate chemical structure. All substructures appearing in $x_D^{Full}$ can be generalized.

In block 930, atomistic details are reintroduced into the remaining substructures. Heteroatoms (e.g., O, S, N, P, F, Cl, Br, etc.) that were replaced with carbon to form generalized substructures can be reintroduced at their proper locations. The heteroatoms placement in the SMILES string can be determined in the backbone structure. Replacement of the atomistic details can be repeated until all atomistic details have been reintroduced.

In block 940, the substructures including the atomistic details can be filtered using generalized substructures lacking bonding details. Using the counts of substructures appearing in $x_D^{Select}$, generated structures can be filtered to eliminate substructures that are not applicable to the generation of later substructures after introduction of the bonding details. Double bonds, triple bonds, and aromatic ring bonds can be reintroduced to the substructures remaining after reintroduction of the atomistic details.

In block 950, bonding details can be reintroduced to the remaining substructures. Double bonds, triple bonds, and aromatic ring bonds that were replaced with single bonds can be reintroduced at their proper locations. Replacement of the bonding details can be repeated until all bonding details have been reintroduced.

In block 960, the set of substructures including all backbone information, atomistic information, and bonding information can be filtered utilizing $x_D^{Full}$ for the full component set.

Structures satisfying both $x_D^{Select}$ and $x_p$ can be obtained.

Figure 10:
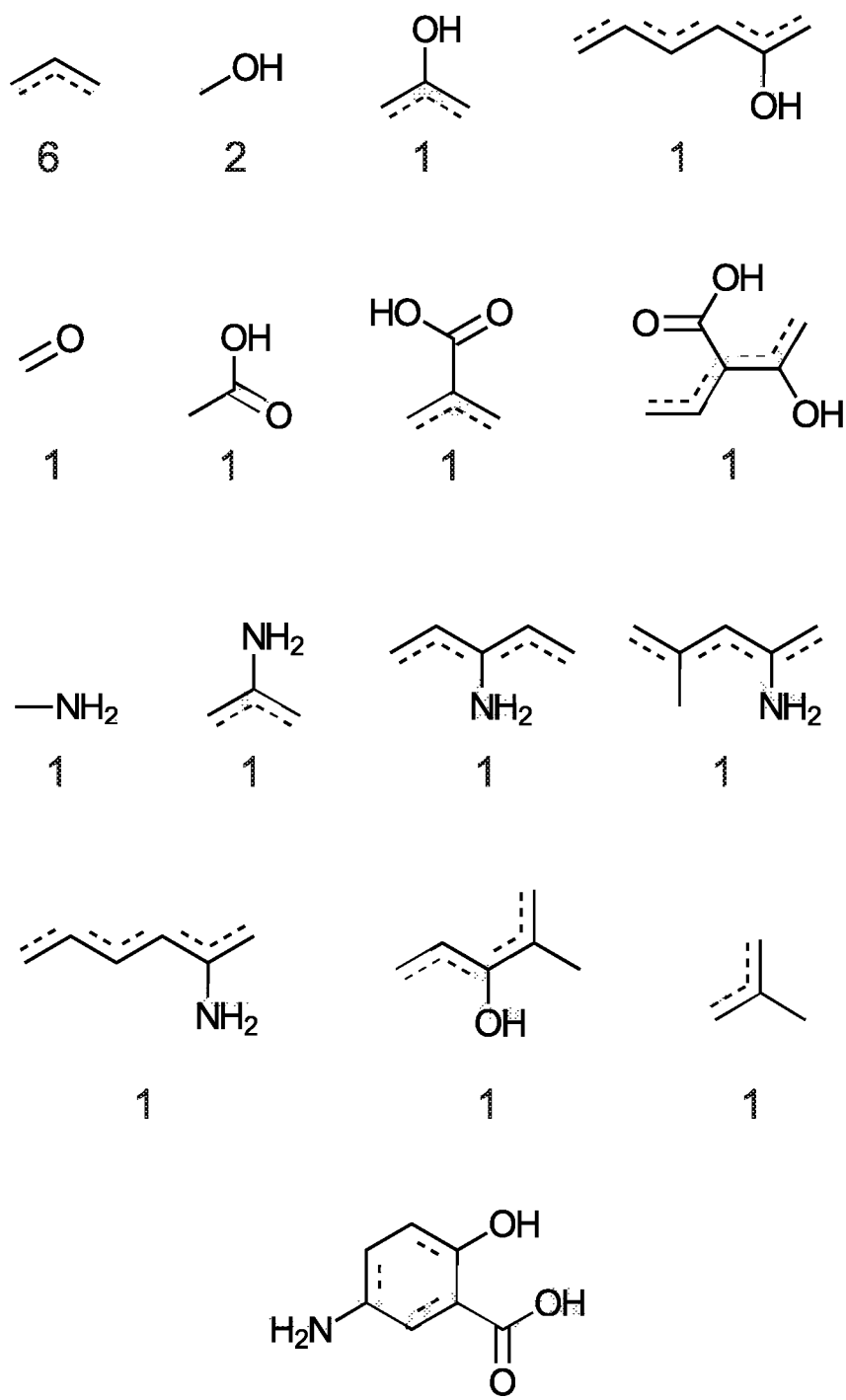
FIG. 10 is a diagram showing a set of possible substructures generated from a known chemical compound for a data-driven feature set, in accordance with an embodiment of the present invention.

FIG. 10 is a diagram showing a set of possible substructures generated from a known chemical compound for a data-driven feature set, in accordance with an embodiment of the present invention.

Each substructure including from 1 to 11 atoms in the original structure can be identified by examining all possible combinations of adjoining atoms making up the chemical compound, and transforming cyclic components into linear or branching arrangements. The number of each substructure identified in the original compound is presented below the substructure. The substructures can form a data-driven substructure set, and the counts can form a data-driven substructure feature vector.

Figure 11:
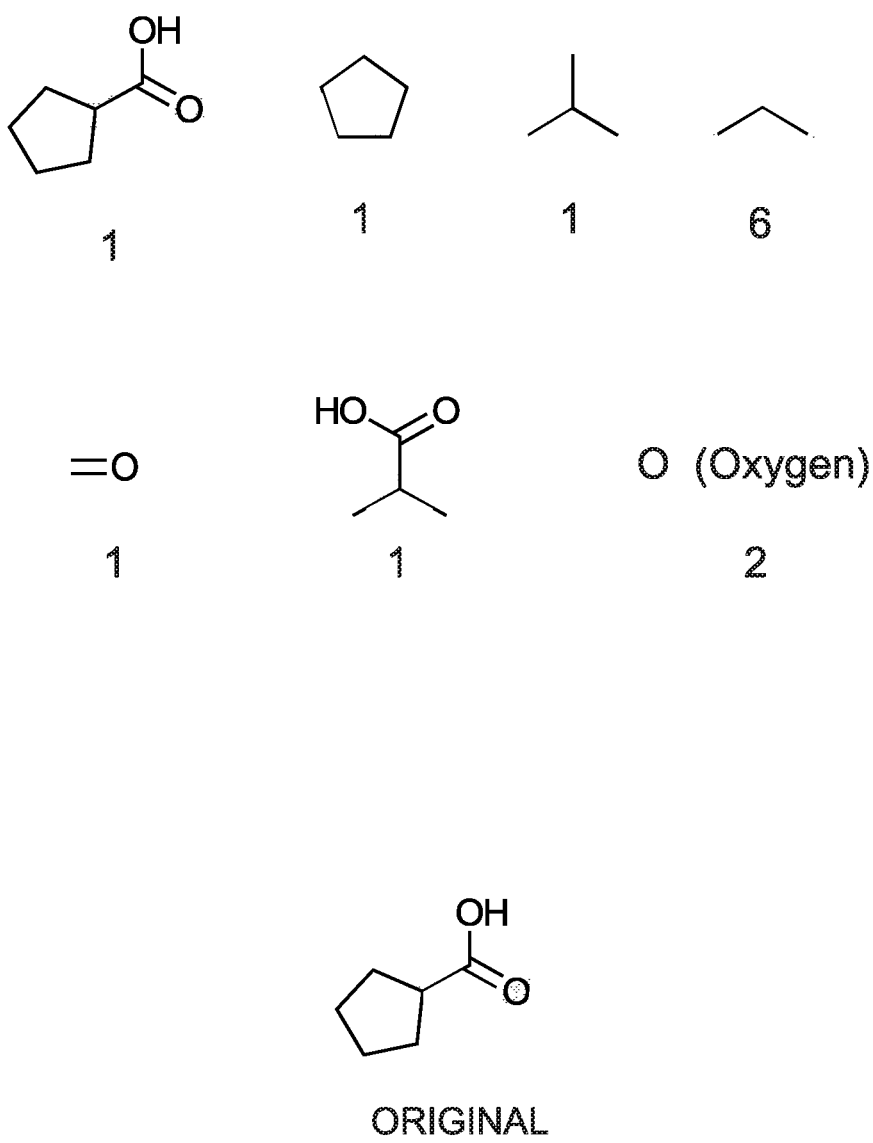
FIG. 11 is a diagram showing a set of possible substructures generated from a known chemical compound for a predetermined feature set, in accordance with an embodiment of the present invention.

FIG. 11 is a diagram showing a set of possible substructures generated from a known chemical compound for a predetermined feature set, in accordance with an embodiment of the present invention.

Utilizing recognized representations of the molecular components from which the original compound can be constructed, a predefined component set and predefined component feature vector can be constructed.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer implemented method of generating new chemical compounds, comprising:
    preparing a data-driven substructure feature vector representing the atoms and bonds of a chemical structure for each of a plurality of chemical compounds for which a chemical or physical property is known;
    preparing a predefined component feature vector representing backbone components, atoms, and chemical bonds;
    creating a regression model to predict a target value for the chemical or physical property;
    performing a search algorithm to identify substructure features that affect the target value for the chemical or physical property;
    generating a candidate structure having the target value for the chemical or physical property; and
    providing to a user the generated candidate structure for synthesizing the candidate structure.

2. The computer implemented method of claim 1, further comprising testing a synthesized candidate structure to determine the actual value for the chemical or physical property.

3. The computer implemented method of claim 1, further comprising receiving input from a user, wherein the input is a selection of one chemical or physical property and the target value for the selected property.

4. The computer implemented method of claim 1, wherein the data-driven substructure feature vector uses simplified molecular-input line-entry system (SMILES) grammar to represent the plurality of chemical compounds, and the predefined component feature vector uses SMILES grammar to represent the predefined chemical substructures.

5. The computer implemented method of claim 1, wherein the regression model is a kernel ridge regression.

6. The computer implemented method of claim 1, wherein the search algorithm utilizes a particle swarm optimization algorithm.

7. The computer implemented method of claim 1, wherein the candidate structure is generated using backbone structuring, atomistic detailing, and bond detailing.

8. The computer implemented method of claim 7, wherein generated candidate structures that do not include specific substructures are eliminated to avoid an exponential increase in generated candidate structures.

9. A non-transitory article of manufacture tangibly embodying a computer readable program which when executed causes a computer to perform the steps of claim 1.

10. A computer implemented method of generating new chemical compounds, comprising:
    receiving input from a user selecting a property from a list of chemical and physical properties;
    receiving input of a target value for the selected property;
    automatically preparing a data-driven substructure feature vector representing the atoms and bonds of a chemical structure for each of a plurality of chemical compounds from a data set of chemical compounds for which the selected property is known;
    preparing a predefined component feature vector from backbone information, atomistic information, and bonding information;
    creating a regression model to predict a resulting value for the selected property;
    perform a search algorithm to identify substructure features that affect the resulting value for the selected property;
    generating a candidate structure having the target value for the selected property;
    synthesizing the candidate structure; and
    testing the synthesized candidate structure to determine the actual value of the selected property.

11. The computer method of claim 10, wherein the data-driven substructure feature vector uses simplified molecular-input line-entry system (SMILES) strings to represent the plurality of chemical compounds.

12. The computer method of claim 11, wherein the candidate structure is generated by combining the information in the data-driven substructure feature vectors and information in the predefined component feature vector.

13. The computer method of claim 12, wherein the candidate structure is generated by concatenating portions of the SMILES strings of the data-driven substructure feature vectors and the predefined component feature vector.

14. The computer method of claim 13, wherein the candidate structure is modified based on regularization.

15. The computer method of claim 14, wherein the number of candidate structures is maintained below a maximum by filtering proposed candidate structures using the data-driven substructures.

16. A non-transitory computer readable storage medium comprising a computer readable program for generating new chemical compounds, wherein the computer readable program when executed on a computer causes the computer to perform the steps of:
    preparing a data-driven substructure feature vector representing the atoms and bonds of a chemical structure for each of a plurality of chemical compounds for which a chemical or physical property is known;
    preparing a predefined component feature vector representing backbone components, atoms, and chemical bonds;
    creating a regression model to predict a target value for the chemical or physical property;
    performing a search algorithm to identify substructure features that affect the target value for the chemical or physical property;
    generating a candidate structure having the target value for the chemical or physical property; and
    providing to a user the generated candidate structure for synthesizing the candidate structure.

17. The non-transitory computer readable storage medium of claim 16, further comprising receiving input from a user, wherein the input is a selection of one chemical or physical property.

18. The non-transitory computer readable storage medium of claim 16, wherein the search algorithm utilizes a particle swarm optimization algorithm.

19. The non-transitory computer readable storage medium of claim 16, wherein the regression model is a kernel ridge regression.

20. The non-transitory computer readable storage medium of claim 16, wherein the predefined component feature vector is based on the number of backbone components, the number of atomistic components, and the number of bond components.

* * * * *